United States Patent
Wilson et al.

(10) Patent No.: US 6,425,898 B1
(45) Date of Patent: *Jul. 30, 2002

(54) DELIVERY APPARATUS FOR A SELF-EXPANDING STENT

(75) Inventors: David J. Wilson, Ft. Lauderdale; Frederick Feller, III, Margate, both of FL (US); Luis A. Davila, Pleasanton, CA (US); Stephen J. Querns, Boca Raton; Kirk L. Johnson, Weston, both of FL (US)

(73) Assignee: Cordis Corporation, Miami, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/243,750

(22) Filed: Feb. 3, 1999

Related U.S. Application Data (63) Continuation-in-part of application No. 09/042,276, filed on Mar. 13, 1998, now Pat. No. 6,019,778.

(51) Int. Cl.$^7$ .................................................. A61F 11/00
(52) U.S. Cl. ....................................... 606/108; 623/1.12
(58) Field of Search ................................ 606/108, 198, 606/184–187, 190–194; 623/11–12, 1.11, 1.12; 604/264, 282, 280

(56) References Cited

U.S. PATENT DOCUMENTS

| | | | |
|---|---|---|---|
| 3,485,234 A | 12/1969 | Stevens | 128/2 |
| 3,585,707 A | 6/1971 | Stevens | 29/427 |
| 3,612,058 A | 10/1971 | Ackerman | 128/348 |
| 4,503,569 A | 3/1985 | Dotter | 3/1.4 |
| 4,516,972 A | 5/1985 | Samson | 604/282 |
| 4,580,568 A | 4/1986 | Gianturco | 128/345 |
| 4,665,771 A | 5/1987 | Mitchell | 74/788 |

(List continued on next page.)

FOREIGN PATENT DOCUMENTS

| | | | |
|---|---|---|---|
| EP | 0 177 330 | 1/1985 | .......... A61M/29/00 |
| EP | 0 696 447 A2 | 2/1996 | |
| EP | 0 941 716 A2 | 9/1999 | |
| WO | WO 96/32078 | 10/1996 | ............. A61F/2/06 |
| WO | WO 97/32623 | 9/1997 | |
| WO | WO 98/10713 | 3/1998 | |
| WO | WO 98/14224 | 4/1998 | |

OTHER PUBLICATIONS

International Search Report dated Jun. 5, 2001 from the European Patent Office.

Primary Examiner—Cary E. O'Connor (57) ABSTRACT

In accordance with the present invention there is provided a delivery apparatus for a self-expanding stent. The apparatus has an outer sheath which is an elongated tubular member with distal and proximal ends and inside and outside diameters. The outer sheath has an enlarged section adjacent its distal end. The enlarged section has a greater inside and outside diameter than the inside and outside diameter of the sheath proximal to the enlarged section. The apparatus also includes an inner shaft located coaxially within the outer sheath. The shaft has a distal end and a proximal end. The shaft further includes a stop attached thereto which is proximal to the distal end of the sheath. Lastly, the apparatus includes a self-expanding stent located within the enlarged section of the outer sheath and makes frictional contact with the outer sheath. The shaft is disposed coaxially within a lumen of the stent, whereby the stent makes contact with the stop during deployment.

28 Claims, 4 Drawing Sheets

U.S. PATENT DOCUMENTS

| | | | |
|---|---|---|---|
| 4,665,905 A | 5/1987 | Brown | 128/80 |
| 4,665,918 A | 5/1987 | Garza | 128/343 |
| 4,676,229 A | 6/1987 | Krasnicki | 128/4 |
| 4,705,511 A | 11/1987 | Kocak | 604/282 |
| 4,732,152 A | 3/1988 | Wallsten | 128/343 |
| 4,733,665 A | 3/1988 | Palmaz | 128/343 |
| 4,768,507 A | 9/1988 | Fischell | 128/303 |
| 4,817,613 A | 4/1989 | Jaraczewski | 128/658 |
| 4,842,590 A | 6/1989 | Tanabae | 604/282 |
| 4,875,468 A | 10/1989 | Krauter | 128/3 |
| 4,898,591 A | 2/1990 | Jang | 604/282 |
| 4,925,445 A | 5/1990 | Sakamoto | 604/95 |
| 4,954,126 A | 9/1990 | Wallsten | 600/36 |
| 4,998,539 A | 3/1991 | Delsanti | 128/898 |
| 5,019,057 A * | 5/1991 | Truckai | 604/282 |
| 5,026,377 A * | 6/1991 | Burton et al. | 606/108 |
| 5,037,427 A | 8/1991 | Harada | 606/108 |
| 5,045,072 A | 9/1991 | Castillo | 604/280 |
| 5,057,092 A | 10/1991 | Webster | 604/282 |
| 5,069,674 A | 12/1991 | Fearnot | 604/282 |
| 5,089,005 A | 2/1992 | Harada | 606/194 |
| 5,160,341 A | 11/1992 | Brenneman | 606/198 |
| 5,190,520 A | 3/1993 | Fenton | 604/43 |
| 5,201,757 A | 4/1993 | Heyn | 606/198 |
| 5,201,901 A | 4/1993 | Harada | 606/198 |
| 5,217,440 A | 6/1993 | Frassica | 604/282 |
| 5,221,270 A | 6/1993 | Parker | 604/282 |
| 5,221,372 A | 6/1993 | Olson | 148/326 |
| 5,254,107 A | 10/1993 | Soltesz | 604/282 |
| 5,279,596 A | 1/1994 | Castaneda | 604/282 |
| 5,290,295 A | 3/1994 | Querals | 606/108 |
| 5,306,252 A | 4/1994 | Yutori | 604/164 |
| 5,354,308 A * | 10/1994 | Simon et al. | 606/198 |
| 5,366,442 A | 11/1994 | Wang | 604/103 |
| 5,415,664 A | 5/1995 | Pinchuk | 606/108 |
| 5,449,373 A | 9/1995 | Pinchasik | 606/198 |
| 5,480,423 A | 1/1996 | Ravenscroft | 623/1 |
| 5,498,240 A * | 3/1996 | Bagaoisan et al. | 604/96 |
| 5,514,154 A | 5/1996 | Lau | 606/195 |
| B14,954,126 A | 5/1996 | Wallsten | 600/36 |
| 5,534,007 A | 7/1996 | St. Germain | 606/108 |
| 5,538,510 A | 7/1996 | Fontrirroche | 604/265 |
| 5,554,139 A * | 9/1996 | Okajima | 604/282 |
| 5,562,641 A | 10/1996 | Flomenblit | 604/281 |
| 5,569,295 A | 10/1996 | Lam | 606/198 |
| 5,571,168 A | 11/1996 | Toro | 623/1 |
| 5,571,170 A | 11/1996 | Palmaz | 623/1 |
| 5,591,197 A | 1/1997 | Orth | 606/198 |
| 5,603,698 A | 2/1997 | Roberts | 604/104 |
| 5,603,721 A | 2/1997 | Lau | 606/195 |
| 5,620,649 A | 4/1997 | Trotta | 264/515 |
| 5,647,857 A * | 7/1997 | Anderson et al. | 604/264 |
| 5,649,952 A | 7/1997 | Lam | 606/198 |
| 5,665,103 A * | 9/1997 | Lafontaine et al. | 606/192 |
| 5,674,208 A | 10/1997 | Berg | 604/282 |
| 5,690,644 A | 11/1997 | Yurek | 606/108 |
| 5,695,499 A | 12/1997 | Helgerson | 606/108 |
| 5,697,971 A | 12/1997 | Fischell | 623/1 |
| 5,700,269 A * | 12/1997 | Pinchuk et al. | 606/108 |
| 5,702,418 A * | 12/1997 | Ravenscroft | 606/108 |
| 5,704,926 A | 1/1998 | Sutton | 604/282 |
| 5,707,376 A | 1/1998 | Kavteladze | 606/108 |
| 5,728,158 A | 3/1998 | Lau | 623/12 |
| 5,735,859 A | 4/1998 | Fischell | 606/108 |
| 5,735,893 A | 4/1998 | Lau | 623/1 |
| 5,755,781 A | 5/1998 | Jayaraman | 623/1 |
| 5,772,669 A * | 6/1998 | Vrba | 606/108 |
| 5,800,517 A * | 9/1998 | Anderson et al. | 606/195 |
| 5,843,090 A * | 12/1998 | Schuetz | 606/108 |
| 5,984,964 A * | 11/1999 | Roberts | 623/1.11 |
| 6,019,778 A * | 2/2000 | Wilson et al. | 606/198 |

* cited by examiner

DELIVERY APPARATUS FOR A SELF-EXPANDING STENT

This application is a continuation-in-part of U.S. patent application Ser. No. 09/042,276 filed Mar. 13, 1998, now U.S. Pat. No. 6,019,778 issued Feb. 1, 2000.

FIELD OF THE INVENTION

The present invention relates to an expandable intraluminal grafts ("stents") for use within a body passageway or duct which are particularly useful for repairing blood vessels narrowed or occluded by disease. The present invention relates even further to systems for delivering such stents.

BACKGROUND OF THE INVENTION

Percutaneous transluminal coronary angioplasty (PTCA) is a therapeutic medical procedure used to increase blood flow through the coronary artery and can often be used as an alternative to coronary by-pass surgery. In this procedure, the angioplasty balloon is inflated within the stenosed vessel, or body passageway, in order to shear and disrupt the wall components of the vessel to obtain an enlarged lumen. With respect to arterial stenosed lesions, the relatively incompressible plaque remains unaltered, while the more elastic medial and adventitial layers of the body passageway stretch around the plaque. This process produces dissection, or a splitting and tearing, of the body passageway wall layers, wherein the intima, or internal surface of the artery or body passageway, suffers fissuring. This dissection forms a "flap" of underlying tissue which may reduce the blood flow through the lumen, or block the lumen. Typically, the distending intraluminal pressure within the body passageway can hold the disrupted layer, or flap, in place. If the intimal flap created by the balloon dilation procedure is not maintained in place against the expanded intima, the intimal flap can fold down into the lumen and close off the lumen, or may even become detached and enter the body passageway. When the intimal flap closes off the body passageway, immediate surgery is necessary to correct this problem.

Recently, transluminal prostheses have been widely used in the medical arts for implantation in blood vessels, biliary ducts, or other similar organs of the living body. These prostheses are commonly known as stents and are used to maintain, open, or dilate tubular structures. An example of a commonly used stent is given in U.S. Pat. No. 4,733,665 filed by Palmaz on Nov. 7, 1985, which is hereby incorporated herein by reference. Such stents are often referred to as balloon expandable stents. Typically the stent is made from a solid tube of stainless steel. Thereafter, a series of cuts are made in the wall of the stent. The stent has a first smaller diameter which permits the stent to be delivered through the human vasculature by being crimped onto a balloon catheter. The stent also has a second, expanded diameter, upon the application, by the balloon catheter, from the interior of the tubular shaped member of a radially, outwardly extending force.

However, such stents are often impractical for use in some vessels such as the carotid artery. The carotid artery is easily accessible from the exterior of the human body, and is often visible by looking at ones neck. A patient having a balloon expandable stent made from stainless steel or the like, placed in their carotid artery might be susceptible to sever injury through day to day activity. A sufficient force placed on the patients neck, such as by falling, could cause the stent to collapse, resulting in injury to the patient. In order to prevent this, self expanding stents have been proposed for use in such vessels. Self expanding stents act like springs and will recover to their expanded or implanted configuration after being crushed.

One type of self-expanding stent is disclosed in U.S. Pat. No. 4,665,771, which stent has a radially and axially flexible, elastic tubular body with a predetermined diameter that is variable under axial movement of ends of the body relative to each other and which is composed of a plurality of individually rigid but flexible and elastic thread elements defining a radially self-expanding helix. This type of stent is known in the art as a "braided stent" and is so designated herein. Placement of such stents in a body vessel can be achieved by a device which comprise an outer catheter for holding the stent at its distal end, and an inner piston which pushes the stent forward once it is in position.

Other types of self-expanding stents use alloys such as Nitinol (Ni—Ti alloy) which have shape memory and/or superelastic characteristics in medical devices which are designed to be inserted into a patient's body. The shape memory characteristics allow the devices to be deformed to facilitate their insertion into a body lumen or cavity and then be heated within the body so that the device returns to its original shape. Superelastic characteristics on the other hand generally allow the metal to be deformed and restrained in the deformed condition to facilitate the insertion of the medical device containing the metal into a patient's body, with such deformation causing the phase transformation. Once within the body lumen the restraint on the superelastic member can be removed, thereby reducing the stress therein so that the superelastic member can return to its original un-deformed shape by the transformation back to the original phase.

Alloys having shape memory/superelastic characteristics generally have at least two phases. These phases are a martensite phase, which has a relatively low tensile strength and which is stable at relatively low temperatures, and an austenite phase, which has a relatively high tensile strength and which is stable at temperatures higher than the martensite phase.

When stress is applied to a specimen of a metal such as Nitinol exhibiting superelastic characteristics at a temperature above which the austenite is stable (i.e. the temperature at which the transformation of martensite phase to the austenite phase is complete), the specimen deforms elastically until it reaches a particular stress level where the alloy then undergoes a stress-induced phase transformation from the austenite phase to the martensite phase. As the phase transformation proceeds, the alloy undergoes significant increases in strain but with little or no corresponding increases in stress. The strain increases while the stress remains essentially constant until the transformation of the austenite phase to the martensite phase is complete. Thereafter, further increases in stress are necessary to cause further deformation. The martensitic metal first deforms elastically upon the application of additional stress and then plastically with permanent residual deformation.

If the load on the specimen is removed before any permanent deformation has occurred, the martensitic specimen will elastically recover and transform back to the austenite phase. The reduction in stress first causes a decrease in strain. As stress reduction reaches the level at which the martensite phase transforms back into the austenite phase, the stress level in the specimen will remain essentially constant (but substantially less than the constant stress level at which the austenite transforms to the martensite) until the transformation back to the austenite phase is complete, i.e. there is significant recovery in strain with only negligible corresponding stress reduction. After the transformation back to austenite is complete, further stress reduction results in elastic strain reduction. This ability to incur significant strain at relatively constant stress upon the application of a load and to recover from the deformation upon the removal of the load is commonly referred to as superelasticity or pseudoelasticity. It is this property of the material which makes it useful in manufacturing tube cut self-expanding stents. The prior art makes reference to the use of metal alloys having superelastic characteristics in medical devices which are intended to be inserted or otherwise used within a patient's body. See for example, U.S. Pat. No. 4,665,905 (Jervis) and U.S. Pat. No. 4,925,445 (Sakamoto et al.).

Designing delivery systems for delivering self-expanding stents has proven some what difficult. One example of a prior art self-expanding stent delivery system is shown in U.S. Pat. No. 4,580,568 issued to Gianturco on Apr. 8, 1986. This reference discloses a delivery apparatus which uses a hollow sheath, like a catheter. The sheath is inserted into a body vessel and navigated therethrough so that its distal end is adjacent the target site. The stent is then compressed to a smaller diameter and loaded into the sheath at the sheath's proximal end. A cylindrical flat end pusher, having a diameter almost equal to the inside diameter of the sheath is inserted into the sheath behind the stent. The pusher is then used to push the stent from the proximal end of the sheath to the distal end of the sheath. Once the stent is at the distal end of the sheath, the sheath is pulled back, while the pusher remain stationary, thereby exposing the stent and expanding it within the vessel.

However, delivering the stent through the entire length of the catheter can cause many problems, including possible damage to a vessel or the stent during its travel. In addition, it is often difficult to design a pusher having enough flexibility to navigate through the catheter, but also enough stiffness to push the stent out of the catheter. Therefore, it was discovered that pre-loading the stent into the distal and of the catheter, and then delivering the catheter through the vessel to the target site may be a better approach. In order to ensure proper placement of the stent within catheter, it is often preferred that the stent be pre-loaded at the manufacturing site. However, pre-loading the stent has also posed some difficulties. Because the catheter exerts a significant force on the self expanding stent which keeps it from expanding, the stent may tend to become imbedded within the inner wall of the catheter. When this happens, the catheter has difficulty sliding over the stent during delivery. This situation can result in the stent becoming stuck inside the catheter, or could damage the stent during delivery.

Another example of a prior art self-expanding stent delivery system is given in U.S. Pat. No. 4,732,152 issued to Wallsten et al. on Mar. 22, 1988. This patent discloses a probe or catheter having a self-expanding stent pre-loaded into its distal end. The stent is first placed within a flexible hose and compressed before it is loaded into the catheter. When the stent is at the delivery site the catheter and hose are withdrawn over the stent so that it can expand within the vessel. However, withdrawing the flexible hose over the stent during expansion could also cause damage to the stent.

For prior art delivery devices, the maximum outside diameter of the device was usually controlled by the diameter of the un-deployed stent located in the device. Typically, the un-deployed stent can only be compressed so much, and therefore its un-deployed diameter determined the maximum diameter of the delivery device. For prior art devices, the diameter of the entire delivery device along its length is substantially uniform. Therefore, the outside diameter along the entire length of the device was its maximum diameter as required by the stent. That is, the overall outer diameter of the outer sheath for these devices is controlled by the size of the pre-loaded stent. As explained below, large sized outer sheaths can pose obstacles to the physician Often a sheath, such as, a guiding catheter, is used with these delivery devices as a conduit into the vasculature. Using fluoroscopy, the physician will often view the targeted site, pre-deployment and post-deployment, of the stent by injecting a radio-opaque solution between the guiding catheter and the delivery device. The ability to view the image is controlled by the injection rate of the solution, which is dependent upon the amount of clearance between the guiding catheter and the outer sheath of the delivery device. A large outer sheath limits the amount of radiopaque solution which can pass through the guiding catheter, causing the physician to have a less clear image of the procedure.

Therefore, there has been a need for a self-expanding stent delivery system which overcomes the above referenced problems associated with prior art delivery systems. Specifically, there has been a need for a self-expanding stent delivery system which allows greater amounts of radiopaque fluid to be passed between the guiding catheter and the outer sheath of the delivery system. The present invention provides such a delivery device.

SUMMARY OF THE INVENTION

In accordance with the present invention there is provided a delivery apparatus for a self-expanding stent. The apparatus has an outer sheath which is an elongated tubular member with distal and proximal ends and inside and outside diameters. The outer sheath has an enlarged section adjacent its distal end. The enlarged section has a greater inside and outside diameter than the inside and outside diameter of the sheath proximal to the enlarged section. The apparatus also includes an inner shaft located coaxially within the outer sheath. The shaft has a distal end and a proximal end. The shaft further includes a stop attached thereto which is proximal to the distal end of the sheath. Lastly, the apparatus includes a self-expanding stent located within the enlarged section of the outer sheath and makes frictional contact with the outer sheath. The shaft is disposed coaxially within a lumen of the stent, whereby the stent makes contact with the stop during deployment.

BRIEF DESCRIPTION OF DRAWINGS

The foregoing and other aspects of the present invention will best be appreciated with reference to the detailed description of the invention in conjunction with the accompanying drawings, wherein.

DETAILED DESCRIPTION OF THE INVENTION

Figures 1, 2:
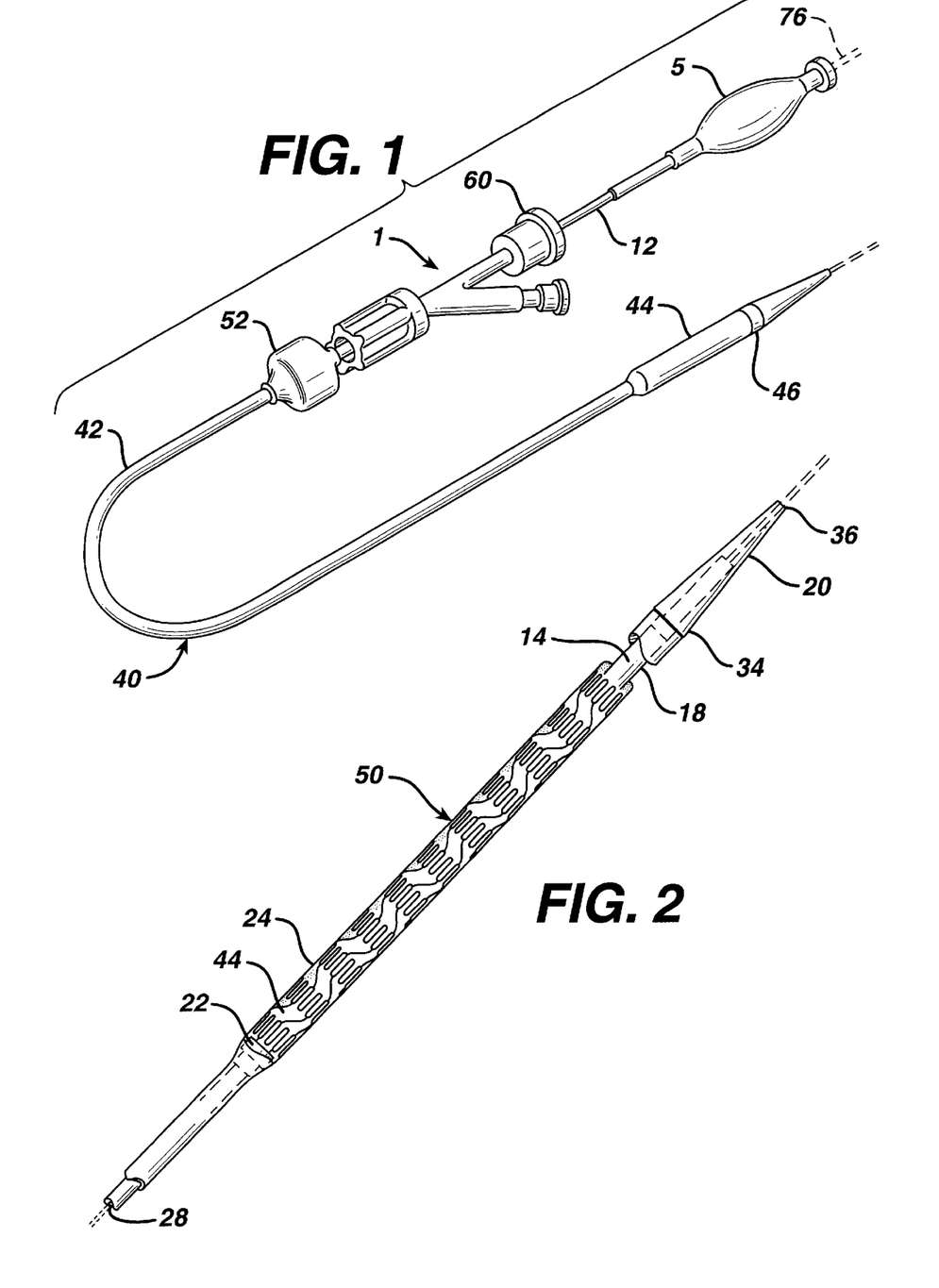
FIG. 1 is a simplified perspective view of a stent delivery apparatus made in accordance with the present invention.
FIG. 2 is a view similar to that of FIG. 1 but showing an enlarged view of the distal end of the apparatus having a section cut away to show the stent loaded therein.
Figure 5:
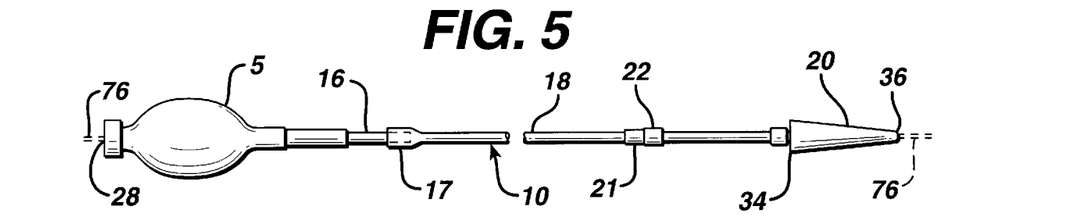
FIG. 5 is a simplified perspective view of the inner shaft of the delivery apparatus made in accordance with the present invention.

Referring now to the figures wherein like numerals indicate the same element throughout the views, there is shown in FIGS. 1 and 2 a self-expanding stent delivery apparatus 1 made in accordance with the present invention. Apparatus 1 comprises inner and outer coaxial tubes. The inner tube is called the shaft 10 and the outer tube is called the sheath 40. Shaft 10 has proximal and distal ends 12 and 14 respectively. The proximal end 12 of the shaft has a Luer guidewire hub 5 attached thereto. As shown in FIG. 5, shaft 10 has a proximal portion 16 which is preferably made from a relatively stiff material such as stainless steel, Nitinol, or any other suitable material known to those of ordinary skill in the art. Shaft 10 also includes a distal portion 18 which is preferably made from a co-extrusion high density polyethylene for the inner portion and polyamide for the outer portion. Other suitable materials for distal portion 18 known to those of ordinary skill in the art include polyurethane, polyimide, polyetheretherketone, and Nitinol. These materials may be utilized as single or multi-layer structures, and may also include reinforcement wires, braid wires, coils, filaments or the like. The two portions are joined together at joint 17 by any number of means known to those of ordinary skill in the art including heat fusing, adhesive bonding, chemical bonding or mechanical attachment. As will become apparent when describing the use of the apparatus, the stainless steel proximal end 16 gives the shaft the necessary rigidity or stiffness it needs to effectively push out the stent, while the distal portion 18 provides the necessary combination of flexibility, to navigate tortuous vessels, and column strength to effectively push out the stent.

The distal portion 14 of the shaft 10 has a distal tip 20 attached thereto. Distal tip 20 can be made from any number of materials known in the art including polyamide, polyurethane, polytetrafluoroethylene, and polyethylene including multi-layer or single layer structures. The distal tip 20 has a proximal end 34 whose diameter is substantially the same as the outer diameter of the sheath 40 which is immediately adjacent thereto. The distal tip tapers to a smaller diameter from its proximal end 34 to its distal end 36, wherein the distal end 36 of the distal tip has a diameter smaller than the inner diameter of the sheath 40. Tip 20 helps to prevent blood from entering the sheath 40 as the apparatus 1 is being navigated through the body vessels. Attached to distal portion 14 of shaft 10 is a stop 22 which is proximal to the distal tip 20 and stent 50. Stop 22 can be made from any number of materials known in the art, including stainless steel, and is even more preferably made from a highly radio-opaque material such as platinum, gold, tantalum, or radio-opaque filled polymer. The stop can be attached to shaft 10 by mechanical or adhesive bonding, or by any other means known to those skilled in the art. Preferably, the diameter of stop 22 is large enough to make sufficient contact with the loaded stent 50 at its end 181 or 182 (FIG. 7) without making frictional contact with the inner layer 48 of the outer sheath 40 (FIG. 8). As will be explained later herein, stop 22 helps to "push" the stent 50 out of the sheath 40 during deployment, by preventing the stent 50 from migrating proximally within the sheath 40 during retraction of the sheath 40 for stent deployment. Proximal to stop 22 is a sleeve 21, which can be made from any number of materials known to those skilled in the art including plastic. Sleeve 21 is attached to shaft 10 immediately proximal to stop 22 by any number of ways known to those skilled in the art including thermal or mechanical bonding. Sleeve 21 acts to reinforce stop 22 during deployment of the stent 50. Sleeve 21 is large enough to make sufficient contact with stop 22 in order to reinforce stop 22. However, it is also preferably small enough not to interfere with the taper of outer sheath 40 when the inner shaft 10 is inside the outer sheath 40. During deployment, the outer sheath 40 is moved in a proximal direction relative to the stationary inner shaft 10. The radio-opaque stop 22 also aides in positioning the stent within the target lesion during deployment within a vessel, as is described below.

A stent bed 24 is defined as being that portion of the shaft between the distal tip 20 and the stop 22 (FIG. 2). The stent bed 24 and the stent 50 are coaxial so that the portion of shaft 18 comprising the stent bed 24 is located within the lumen of stent 50. The stent bed 24 makes minimal contact with stent 50 because of the space which exists between the inner shaft 10 and the outer sheath 40. As the stent is subjected to temperatures at the austenite phase transformation it attempts to recover to its programmed shape by moving outwardly in a radial direction within the sheath. The outer sheath 40 constrains the stent as will be explained later herein.

Figure 6:
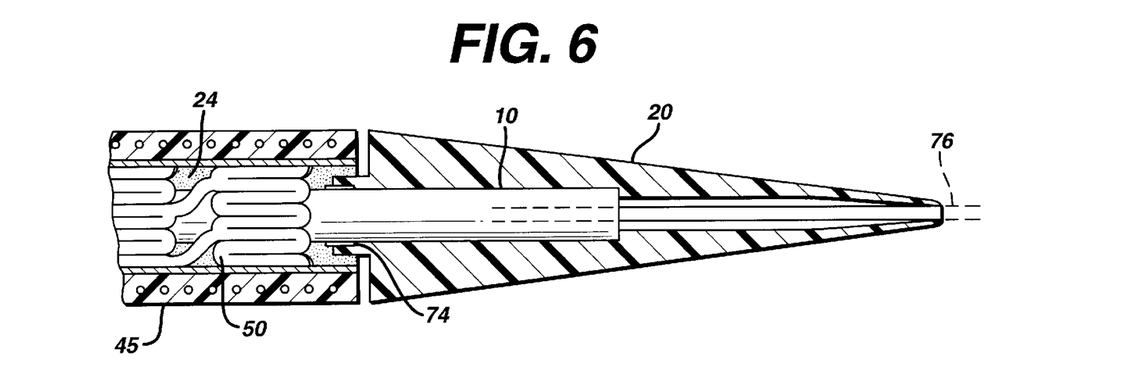
FIG. 6 is a detailed view of FIG. 4 showing a cross-sectional view of the extreme distal end of the delivery device with a stent loaded therein

Distal to the distal end of the loaded stent 50 attached to the inner shaft 10 is a radio-opaque marker 74 (FIG. 6) which can be made of platinum, iridium coated platinum, gold, tantalum, stainless steel or any other suitable material known in the art. Lastly, shaft 10 has a guidewire lumen 28 extending along its length, where the guidewire enters through the guidewire hub 5 and exits through its distal tip 20 (FIGS. 5 and 6). This allows the shaft 10 to receive a guidewire 76 much in the same way that a balloon angioplasty catheter receives a guidewire. Such guidewires are well known in the art and help to guide catheters and other medical devices through the vasculature of the body.

Alternatively, the shaft 10 of the present invention may comprise three tubing sections (proximal shaft, distal shaft, and distal tip). The proximal shaft may be constructed of 304 stainless steel hypo-tubing (O.D.=0.032" and wall thickness=0.0045") and be approximately 12 inches long. The proximal end of the proximal shaft is attached to a typical medical luer connector or "hub". Use of the stainless hypotubing will provide the necessary stiffness and column strength to support the system while the outer sheath is retracted for stent deployment. The distal shaft may be constructed of a coextruded tube consisting of an outer layer of nylon-12 (or another suitable polymer) and an inner layer of a maleated high-density polyethylene such as PLEXAR PX209, sold by the Quantum Chemical Company. PLEXAR PX209 is a maleated high-density polyethylene that chemically bonds to nylon-12 in the extrusion process. The distal shaft is designed to take advantage of the properties of nylon-12 while providing a lubricous inner lumen for tracking over a guidewire. Also, PLEXAR PX209 polymer bonds tenaciously to stainless steel in a typical heat fusing process. U.S. Pat. No. 5,538,510, issued on Jul. 23, 1996, which is hereby incorporated herein by reference, discloses the use of such materials in manufacturing catheters. The distal tip of the inner member may be sealed or insert molded to the distal shaft and constructed of an approximate 25D Shore hardness polyamide elastomer or equivalent. Use of nylon-12 as the outer layer of the distal shaft helps to facilitate this seal. The tip is designed to be a traumatic which can be beneficial when working in the carotid region. Being soft and relatively sticky, the tip may be coated with a hydrophilic coating to provide better lubricity.

Figure 3:
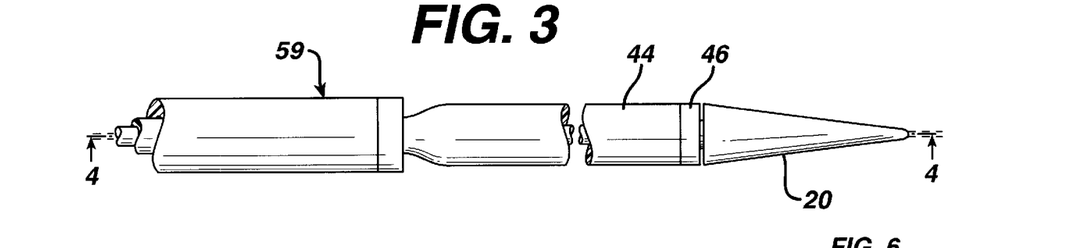
FIG. 3 is a simplified perspective view of the distal end of the delivery apparatus extending outside a guiding catheter, or sheath 59.

Sheath 40 is preferably a polymeric catheter and has a proximal end 42 terminating at a Luer hub 52 (FIG. 1). Sheath 40 also has a distal end 45 which terminates at the proximal end 34 of distal tip 20 of the shaft 10, when the stent 50 is in un-deployed position as shown in FIG. 2. The distal end 45 of sheath 40 includes a radio-opaque marker band 46 disposed along its outer surface (FIGS. 1 and 3). As will be explained below, the stent is fully deployed when the marker band 46 is proximal to radio-opaque stop 22, thus indicating to the physician that it is now safe to remove the apparatus 1 from the body.

Figure 4:
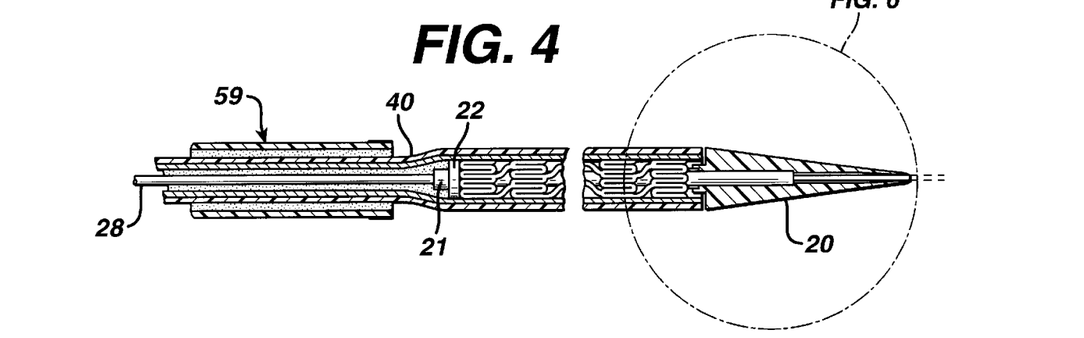
FIG. 4 is a cross-sectional view of FIG. 3 taken along lines 4—4.

As detailed in FIGS. 1 through 4, the distal end 45 of sheath 40 includes an enlarged section 44. Enlarged section 44 has larger inside and outside diameters than the inside and outside diameters of the sheath proximal to section 44. Enlarged section 44 houses the pre-loaded stent 50, the stop 22, sleeve 21, and the stent bed 24. Proximal to sleeve 21, the outer sheath 40 tapers proximally to a smaller size diameter. One particular advantage to this invention can best be described by referring to FIGS. 3 and 4. As seen in those drawings, the reduction in the size of the outer diameter of sheath 40 proximal to enlarged section 44 results in an increase in the clearance between the delivery device 1 and the guiding catheter 59. Using fluoroscopy, the physician will view an image of the target site within the vessel, before and after deployment of the stent, by injecting a radiopaque solution through catheter 59 with the delivery device 1 inside catheter 59. Because the clearance between the outer sheath 40, and catheter 59 is increased by tapering or reducing the outer diameter of the sheath proximal to section 44, higher injection rates are achieved, resulting in better images of the target site for the physician. The tapering of sheath 40 provides higher injection rates of radiopaque fluid, both before and after deployment of the stent, whether section 44 is placed inside the catheter 59, or just distal to catheter 59 as shown in FIGS. 3 and 4.

Often self-expanding delivery systems had problems with the stent becoming embedded within the sheath or catheter in which it is disposed. By referring to FIG. 8, one can see how one embodiment of the present invention solves this problem. Sheath 40 preferably comprises an outer polymer, preferably polyamide, layer 72 and an inner polymer, preferably polytetrafluroethylene, layer 48. Other suitable polymers for the inner and outer layers 48 and 72 include any suitable material known to those skilled in the art including polyethylene, or polyamide, respectively. Positioned between outer and inner layers 72 and 48, respectively, is a wire reinforcing layer 70, which is preferably a braided wire. Braided reinforcing layer 70 is preferably made from stainless steel. The use of braiding reinforcing layers in other types of medical devices can be found in U.S. Pat. No. 3,585,707 issued to Stevens on Jun. 22, 1971, U.S. Pat. No. 5,045,072 issued to Castillo et al. on Sep. 3, 1991, and U.S. Pat. No. 5,254,107 issued to Soltesz on Oct. 19, 1993, all of which are hereby incorporated herein by reference.

Sheath 40 is a composite structure incorporating an inner polytetrafluoroethylene layer 48, an outer polyamide layer 72, and a middle stainless steel braid wire layer 70. The outer sheath 40 can incorporate a single outer polyamide layer 72 from proximal end 42 to its distal end 45 or can be a series of fused transitions decreasing in material durometer from proximal end 42 to distal end 45 along outer layer 72 of sheath 40. The inclusion of transitions of varying material durometers can effectively enhance the catheter performance as it is pushed over the guidewire 76 through the vascular anatomy. The flexibility of the delivery system from proximal end 42 to distal end 45 of sheath 40 can improve the manner in which the system tracks over the guidewire 76.

Layers 48, 70, and 72 of sheath 40 collectively enhance stent 50 deployment. Layers 48 and 70 help to prevent the stent 50 from becoming too imbedded into sheath 40, prior to stent deployment. The braid layer 70 provides radial support to inner layer 48 creating sufficient resistance to the outward radial force of stent 50 within sheath 40. Inner layer 48 also provides a low coefficient of friction surface to reduce the forces required to deploy the stent 50. In addition to the above mentioned benefit, layer 70 offers many other advantages. Layer 70 gives the sheath better pushability, the ability to transmit a force applied by the physician at a proximal location 42 on sheath 40 to the distal tip 20, which aids in navigation across tight stenotic lesions within the vascular anatomy. Layer 70 also gives the sheath better resistance to elongation and necking as a result of tensile loading during sheath retraction for stent deployment. The configuration of braid layer 70 can be changed to change system performance. This is achieved by changing the pitch of the braid, the shape of the individual braid wires, the number of braid wires, and the braid wire diameter. Additionally, coils could be incorporated similarly to layer 70 of sheath 40 to minimize stent imbedment and enhance system flexibility. Use of coils in other types of catheters can be found in U.S. Pat. No. 5,279,596 issued to Castaneda et al. on Jan. 18, 1994, which is hereby incorporated herein by reference.

Many prior art self-expanding stent delivery systems did not use braid layers and there may be many reasons why others have not tried this. Because of the size of most self-expanding stents are quite large, as compared to balloon expandable coronary stents, the diameters of the delivery devices had to be large as well. However, it is always advantageous to have catheters or delivery systems which are as small as possible. This is so the devices can reach into smaller vessels, and so that less trauma is caused to the patient. Thus others would have been led away from using such a layer. However, it has been found that even a very thin braid layer in a stent delivery apparatus offers such an advantage, that any incremental increase in the size of the catheter is worth it.

Alternatively, the outer sheath of the system may comprise three tubing sections (proximal sheath, distal sheath, and distal end). The proximal sheath may be constructed of 304 stainless steel hypo-tubing (O.D.=0.065", I.D. 0.053") and be approximately 20 inches long. The proximal end of the proximal shaft is attached to a valve that provides a seal to blood flow when closed, and allows free movement over the inner member when opened. Again, the use of stainless steel for the proximal end will give the physician the necessary stiffness and column strength to manipulate the system for deployment. The distal sheath of the outer member is also constructed of a coextruded tube of nylon-12 over the PLEXAR PX209 polymer. The same logic used above applies. We need lubricity over the inner member (provided by the PLEXAR PX209 polymer) and the push and tracking ability of nylon-12. The distal shaft is again heat fused to the stainless steel hypotube.

FIGS. 1 and 2 show the stent 50 as being in its fully un-deployed position. This is the position the stent is in when the apparatus 1 is inserted into the vasculature and its distal end is navigated to a target site. Stent 50 is disposed around the stent bed 24 and at the distal end 45 of sheath 40. The distal tip 20 of the shaft 10 is distal to the distal end 45 of the sheath 40. The stent 50 is in a compressed state and makes frictional contact with the inner surface 48 of the sheath 40.

When being inserted into a patient, sheath 40 and shaft 10 are locked together at their proximal ends by a Tuohy Borst valve 60. This prevents any sliding movement between the shaft and sheath which could result in a premature deployment or partial deployment of the stent. When the stent 50 reaches its target site and is ready for deployment, the Tuohy Borst valve 60 is opened so that the sheath 40 and shaft 10 are no longer locked together.

Figure 8:
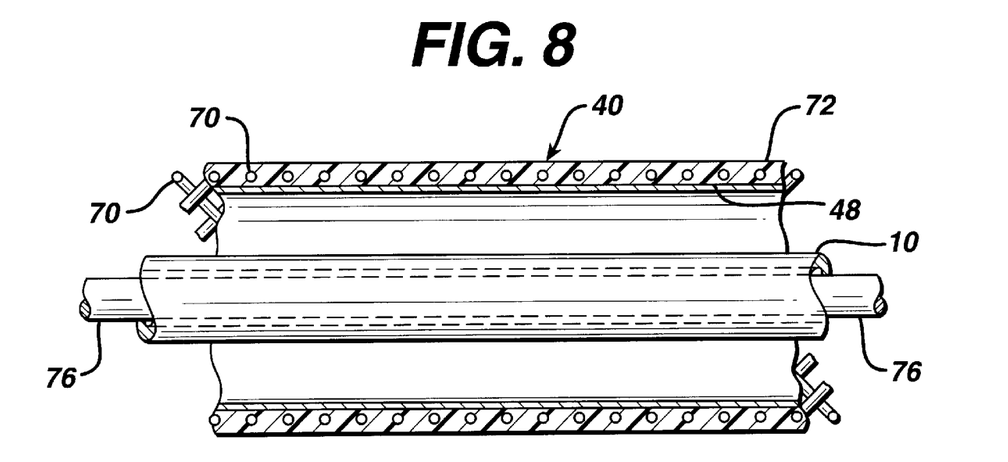
FIG. 8 is a partial cross-sectional view of the inner shaft and outer sheath.
Figure 9:
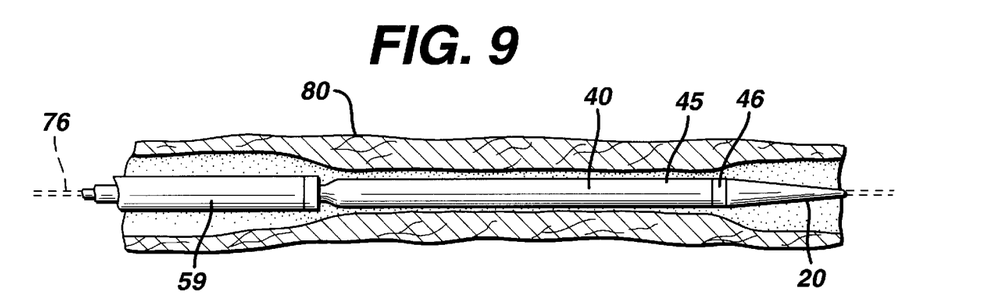
FIGS. 9 through 12 are partial cross-sectional views of the apparatus of the present invention showing the deployment of the self expanding stent within the vasculature.
Figure 10:
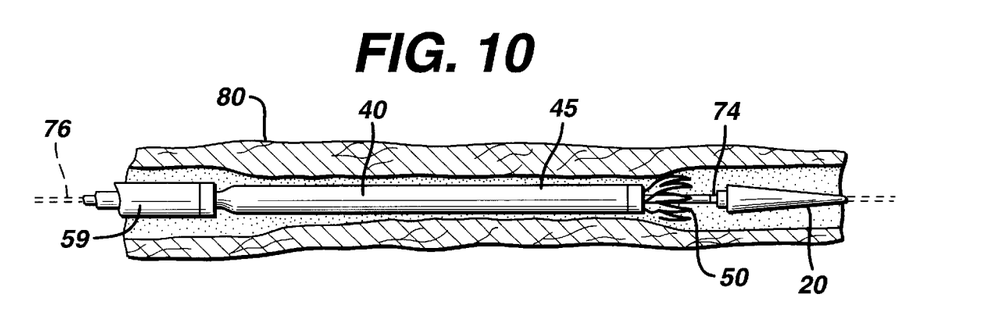
Figure 11:
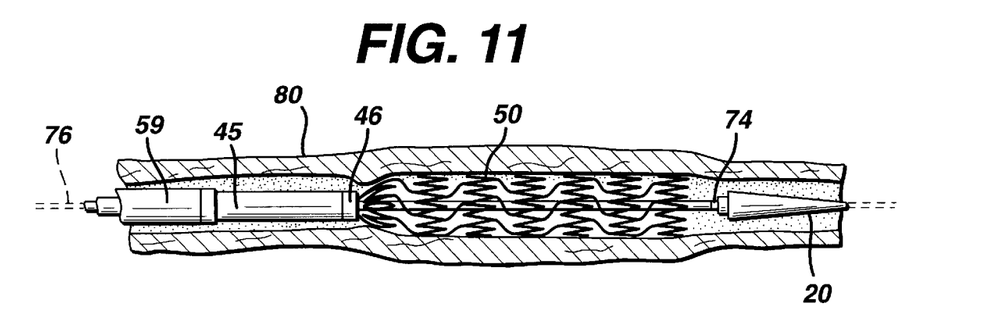
Figure 12:
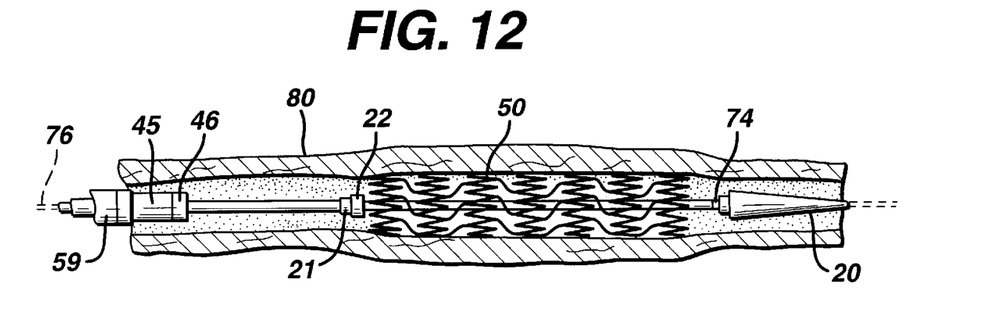

The method under which apparatus 1 deploys stent 50 can best be described by referring to FIGS. 9–12. In FIG. 9, the apparatus 1 has been inserted into a vessel 80 so that so that the stent bed 24 is at a target diseased site. Once the physician determines that the distal marker 74 and proximal marker 22 on shaft 10 indicating the ends of stent 50 are sufficiently placed about the target disease site, the physician would open Tuohy Borst valve 60. The physician would then grasp the proximal end 12 or proximal hub 5 of shaft 10 so as to hold shaft 10 in a fixed position. Thereafter, the physician would grasp the Tuohy valve 60 attached proximally to outer sheath 40 and slide it proximal, relative to the shaft 10 as shown in FIGS. 8 and 9. Stop 22 prevents the stent 50 from sliding back with sheath 40, so that as the sheath 40 is moved back, the stent 50 is effectively pushed out of the distal end 45 of the sheath 40. Stent 50 should be deployed in a distal to proximal direction to minimize the potential for creating emboli with the diseased vessel 80. Stent deployment is complete when the radio-opaque band 46 on the sheath 40 is proximal to radio-opaque stop 22, as shown in FIG. 10. The apparatus 1 can now be withdrawn through stent 50 and removed from the patient.

Figure 7:
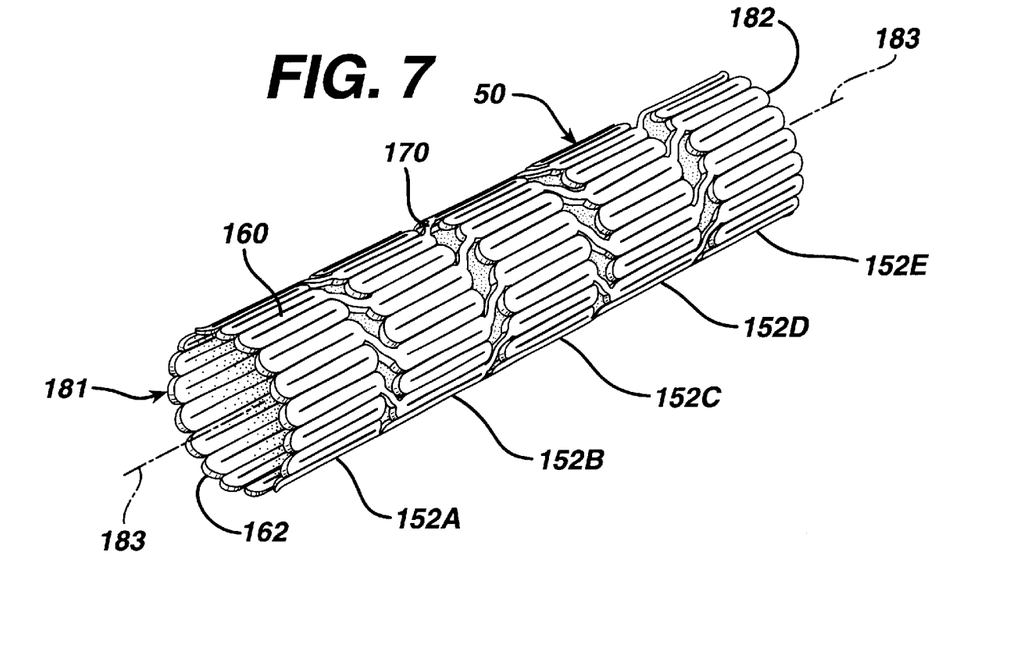
FIG. 7 is a perspective view of the constrained self expanding stent.

FIG. 7 shows a preferred embodiment of a stent 50 which can be used with the present invention. Stent 50 is shown in its un-expanded compressed state, before it is deployed. Stent 50 is preferably made from a superelastic alloy such as Nitinol. Most preferably, stent 50 is made from an alloy comprising from about 50.5% (as used herein these percentages refer to atomic percentages) Ni to about 60% Ni, and most preferably about 55% Ni, with the remainder of the alloy Ti. Preferably, the stent is such that it is superelastic at body temperature, and preferably has an Af in the range from about 24° C. to about 37° C. The superelastic design of the stent makes it crush recoverable which, as discussed above, can be used as a stent or frame for any number of vascular devices for different applications.

Stent 50 is a tubular member having front and back open ends 181 and 182 and a longitudinal axis 183 extending there between. The tubular member has a first smaller diameter, FIG. 9, for insertion into a patient and navigation through the vessels, and a second larger diameter, FIGS. 10–12, for deployment into the target area of a vessel. The tubular member is made from a plurality of adjacent hoops 152, FIG. 7 showing hoops 152(a)–152(e), extending between the front and back ends 181 and 182. The hoops 152 include a plurality of longitudinal struts 160 and a plurality of loops 162 connecting adjacent struts, wherein adjacent struts are connected at opposite ends so as to form an S or Z shape pattern. Stent 50 further includes a plurality of curved bridges 170 which connect adjacent hoops 152.

Bridges 170 connect adjacent struts together at bridge to loop connection points which are offset from the center of a loop.

The above described geometry helps to better distribute strain throughout the stent, prevents metal to metal contact when the stent is bent, and minimizes the opening size between the features, struts, loops and bridges. The number of and nature of the design of the struts, loops and bridges are important factors when determining the working properties and fatigue life properties of the stent. Preferably, each hoop has between 24 to 36 or more struts. Preferably the stent has a ratio of number of struts per hoop to strut length (in inches) which is greater than 200. The length of a strut is measured in its compressed state parallel to the longitudinal axis of the stent.

In trying to minimize the maximum strain experienced by features, the stent utilizes structural geometry's which distribute strain to areas of the stent which are less susceptible to failure than others. For example, one vulnerable area of the stent is the inside radius of the connecting loops. The connecting loops undergo the most deformation of all the stent features. The inside radius of the loop would normally be the area with the highest level of strain on the stent. This area is also critical in that it is usually the smallest radius on the stent. Stress concentrations are generally controlled or minimized by maintaining the largest radii possible. Similarly, we want to minimize local strain concentrations on the bridge and bridge to loop connection points. One way to accomplish this is to utilize the largest possible radii while maintaining feature widths which are consistent with applied forces. Another consideration is to minimize the maximum open area of the stent. Efficient utilization of the original tube from which the stent is cut increases stent strength and it's ability to trap embolic material.

Although particular embodiments of the present invention have been shown and described, modification may be made to the device and/or method without departing from the spirit and scope of the present invention. The terms used in describing the invention are used in their descriptive sense and not as terms of limitations.

That which is claimed is:

1. A delivery apparatus for a self-expanding stent, said apparatus comprising:
   a) a sheath including an elongated substantially tubular member having distal and proximal ends, a proximal section having a first outside diameter, an enlarged section proximate said distal end having a second outside diameter, the second outside diameter being greater than the first outside diameter, said sheath having an increasing durometer along its length from its distal end to its proximal end;
   b) a shaft located coaxially within said sheath, said shaft having a distal end and a proximal end, said shaft further including a radiopaque stop attached thereto, said stop being positioned proximate to said distal end of said sheath;
   c) a radiopaque fluid injection annular gap extending between a guiding catherer having an inside diameter greater than the first outside diameter of said proximal section of said sheath; and
   d) a self-expanding stent located within said enlarged section of said sheath, said stent making frictional contact with said sheath, said shaft disposed coaxially within a lumen of said stent, whereby said stent makes contact with said stop during deployment of said stent.

2. The delivery apparatus of claim 1 wherein said sheath comprises an outer polymeric layer, and inner polymeric layer, and a wire reinforcing layer between said inner and outer layers, said reinforcing layer being more rigid than said inner and outer layers.

3. The apparatus of claim 2 wherein said wire reinforcing layer comprises braids of metallic wire.

4. The apparatus of claim 3 wherein said wire comprises stainless steel.

5. The delivery apparatus of claim 1, wherein said distal end of said shaft extends distal to said distal end of said sheath, and said proximal end of said shaft extends proximal to said proximal end of said sheath.

6. The apparatus of claim 1 wherein said stop makes no substantial frictional contact with said sheath.

7. The apparatus of claim 1 wherein said shaft has a proximal portion made from a metallic material.

8. The apparatus of claim 7 wherein said proximal portion is made from material selected from a group comprising: stainless steel, nickel titanium alloys.

9. The apparatus of claim 1 wherein said stent is made from a superelastic nickel-titanium alloy.

10. The apparatus of claim 1 wherein said shaft further includes a distal tip, said distal tip has a proximal end having an outer diameter which is not less than an outer diameter of said sheath.

11. The apparatus of claim 10 wherein said distal tip is radiopaque.

12. The apparatus of claim 1 wherein said distal end of said shaft has a radio-opaque marker disposed thereon.

13. The apparatus of claim 1 wherein said sheath has an increasing durometer along its length from its distal end to its proximal end.

14. The apparatus according to claim 1 wherein said shaft further includes a reinforcing sleeve attached to said shaft immediately proximal to said stop.

15. A delivery apparatus for a self-expanding stent, said apparatus comprising:
   a) a sheath comprising an elongated tubular member having distal and proximal ends, a proximal section having a first outside diameter, an enlarged section proximate said distal end having a second outside diameter and a tapered section therebetween, the second outside diameter being greater than the first outside diameter, said sheath having an increasing durometer along its length from its distal end to its proximal end;
   b) a shaft located coaxially within said sheath, said shaft having a distal end and a proximal end, said shaft further including a radiopaue stop attached thereto, said stop being positioned proximate to said distal end of said sheath;
   c) a radiopaque fluid injection annular gap extending between a guiding catherer having an inside diameter greater than the first outside diameter of said proximal section of said sheath; and
   d) a self-expanding stent located within said enlarged section of said sheath, said stent making frictional contact with said sheath, said shaft disposed coaxially within a lumen of said stent, whereby said stent makes contact with said stop during deployment of said stent.

16. A delivery apparatus for a self-expanding stent, said apparatus comprising:
   a) a sheath comprising an elongated tubular member having distal and proximal ends, a proximal section having a first outside diameter, an enlarged section proximate said distal end having a second outside diameter and a tapered section therebetween, the second outside diameter being greater than the first outside diameter;
   b) a shaft located coaxially within said sheath, said shaft having a distal end and a proximal end, said shaft further including a radiopaue stop attached thereto, said stop being positioned proximate to said distal end of said sheath;
   c) a radiopaque fluid injection annular gap extending between a guiding catheter having an inside diameter greater than the first outside diameter of said proximal section of said sheath; and
   d) a self-expanding stent located within said enlarged section of said sheath, said stent making frictional contact with said sheath, said shaft disposed coaxially within a lumen of said stent, whereby said stent makes contact with said stop during deployment of said stent.

17. The delivery apparatus of claim 16 wherein said sheath comprises an outer polymeric layer, and inner polymeric layer, and a wire reinforcing layer between said inner and outer layers, said reinforcing layer being more rigid than said inner and outer layers.

18. The apparatus of claim 17 wherein said wire reinforcing layer comprises braids of metallic wire.

19. The apparatus of claim 17 wherein said wire comprises stainless steel.

20. The delivery apparatus of claim 16, wherein said distal end of said shaft extends distal to said distal end of said sheath, and said proximal end of said shaft extends proximal to said proximal end of said sheath.

21. The apparatus of claim 16 wherein said stop makes no substantial frictional contact with said sheath.

22. The apparatus of claim 16 wherein said shaft has a proximal portion made from a metallic material.

23. The apparatus of claim 22 wherein said proximal portion is made from material selected from a group comprising stainless steel, nickel titanium alloys.

24. The apparatus of claim 16 wherein said stent is made from a superelastic nickel-titanium alloy.

25. The apparatus of claim 16 wherein said shaft further includes a distal tip, said distal tip has a proximal end having an outer diameter which is not less than an outer diameter of said sheath.

26. The apparatus of claim 25 wherein said distal tip is radiopaque.

27. The apparatus of claim 16 wherein said distal end of said shaft has a radio-opaque marker disposed thereon.

28. The apparatus of claim 16 wherein said sheath has an increasing durometer along its length from its distal end to its proximal end.

* * * * *